Figure 1:
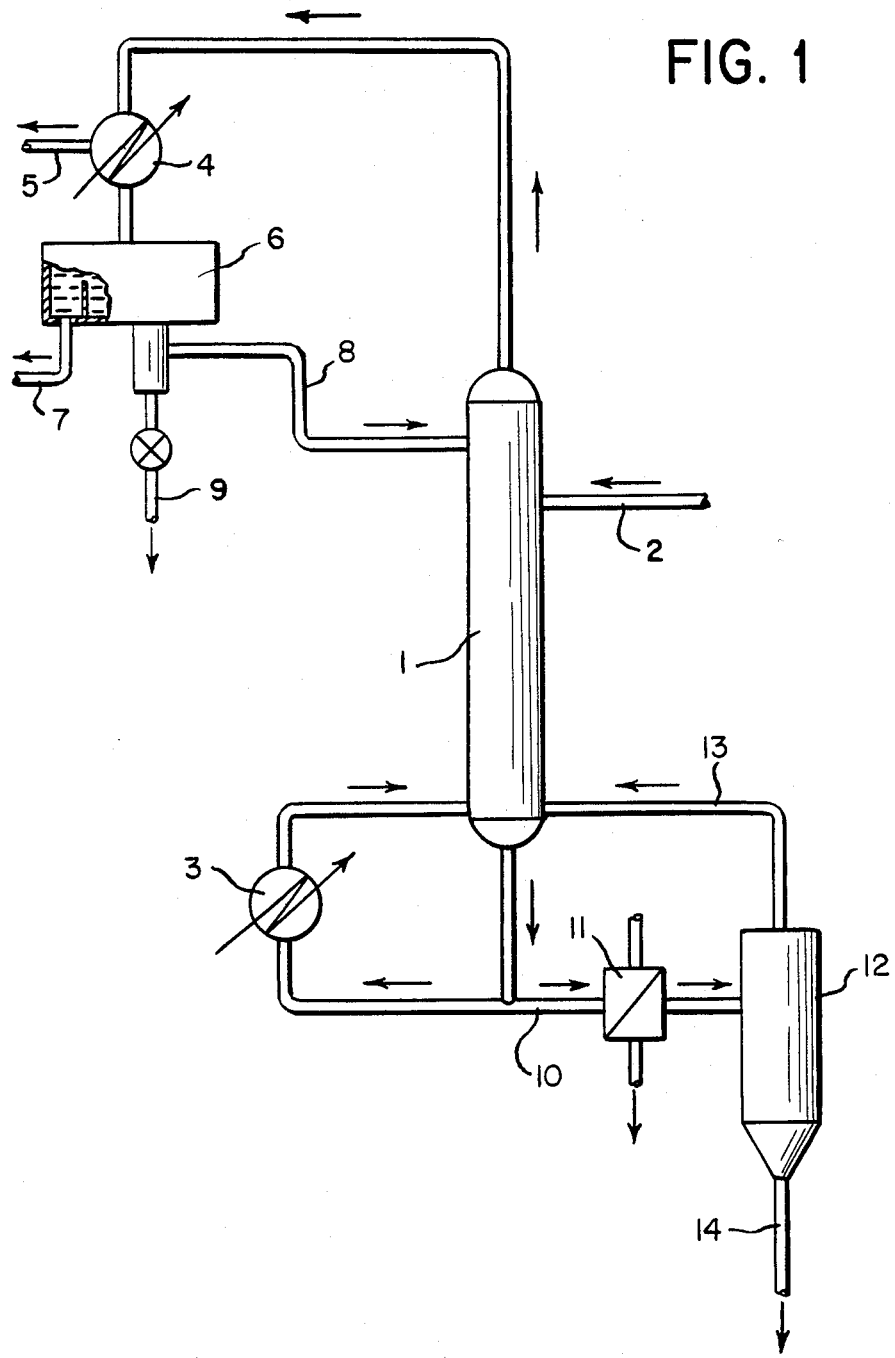

United States Patent [19]

Devic

[11] Patent Number: 4,496,760

[45] Date of Patent: Jan. 29, 1985

[54] PROCESS OF DECOMPOSITION OF A COMPLEX OF ORTHO-BENZOYL BENZOIC ACID, HYDROGEN FLUORIDE AND BORON TRIFLUORIDE

[75] Inventor: Michel Devic, Lyons, France

[73] Assignee: PCUK Produits Chimiques Ugine Kuhlmann, Courbevoie, France

[21] Appl. No.: 523,945

[22] Filed: Aug. 17, 1983

[30] Foreign Application Priority Data

Sep. 1, 1982 [FR] France .............................. 82 14920

[51] Int. Cl.³ .............................................. C07C 59/76
[52] U.S. Cl. ..................................... 562/460; 203/34; 203/67; 423/293; 423/483; 560/52
[58] Field of Search .................. 423/483, 293; 203/34, 203/67; 568/411; 562/460; 560/52

[56] References Cited

U.S. PATENT DOCUMENTS

| | | | |
|---|---|---|---|
| 2,174,118 | 9/1939 | Calcott | 423/483 |
| 2,386,798 | 10/1945 | Hughes | 423/483 |
| 2,468,681 | 4/1949 | McBride | 423/483 |
| 2,534,017 | 1/1950 | Gresham et al. | 423/293 |
| 3,108,131 | 10/1963 | Cohen et al. | 560/52 |
| 3,110,724 | 11/1963 | Woodbridge et al. | 560/52 |
| 3,745,093 | 7/1973 | Lee | 568/411 |
| 3,988,424 | 10/1976 | Fujiyama et al. | 423/483 |
| 4,318,854 | 3/1982 | Trybulski | 260/326 |
| 4,379,092 | 4/1983 | Devic | 260/369 |

FOREIGN PATENT DOCUMENTS

| | | | |
|---|---|---|---|
| 526912 | 6/1956 | Canada | 423/293 |
| 814838 | 6/1937 | France | |
| 486886 | 7/1938 | United Kingdom | |
| 501670 | 3/1939 | United Kingdom | |
| 605472 | 7/1948 | United Kingdom | 423/483 |

OTHER PUBLICATIONS

Charles W. Deane, "The Correlation of Reaction Rates with Acidity Function", J. Am. Chem. Soc., Feb. 1945, pp. 331, vol. 67.

Paul R. Jones, "Ring Chain Tautomerism", Chem. Reviews, vol. 63, 1963, p. 480.

Primary Examiner—Gary P. Straub
Assistant Examiner—Jackson Leeds
Attorney, Agent, or Firm—Pennie & Edmonds

[57] ABSTRACT

A process for the decomposition of complexes of ortho-benzoyl benzoic acids, hydrogen fluoride, and boron trifluoride, whether or not the ortho-benzoyl benzoic acid is substituted, is disclosed wherein the ortho-benzoyl benzoic acid is obtained separately from the hydrogen fluoride and boron trifluoride. This process is characterized in that the complex is treated with an inert solvent at a temperature of at least 20° C., in a distillation column having at least about 8 theoretical plates whereby the solvent reflux is operated at a rate equal to about 5 to about 40 times the weight of the feed delivery rate of the column.

The process of the present invention also makes it possible to recover hydrogen fluoride and boron trifluoride for reuse as catalysts in the synthesis of ortho-benzoyl benzoic acid without causing decomposition of the acid.

22 Claims, 2 Drawing Figures

PROCESS OF DECOMPOSITION OF A COMPLEX OF ORTHO-BENZOYL BENZOIC ACID, HYDROGEN FLUORIDE AND BORON TRIFLUORIDE

TECHNICAL FIELD

This invention relates to a process for the decomposition of complexes, the combination of ortho-benzoyl benzoic acid (OBB acid), substituted with other groups or unsubstituted, hydrofluoric acid (HF), and boron trifluoride ($BF_3$).

BACKGROUND OF THE INVENTION

OBB complexes have a general formula of:

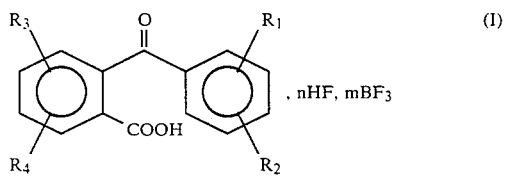

(I)

wherein $R_1$, $R_2$, $R_3$, $R_4$ represent hydrogen, a halogen atom, or a straight chain or branched chain alkyl group of 1 to 5 carbon atoms, and n and m are integers between 1 and 6.

These complexes can be synthesized according to applicant's U.S. Pat. No. 4,397,092.

In order to isolate OBB acid, these complexes may undergo a treatment with boiling water or dilute alkali to destroy the HF and $BF_3$. Recovery of the HF/$BF_3$ combination catalysts, which are used in the synthesis of these complexes from anthraquinone as described in applicant's above-mentioned patent, cannot be performed economically.

These complexes can also be decomposed by heating at 150° to 200° C. over an extended period of time, but such treatment simultaneously causes an almost total degradation of the OBB acid itself. Also, any water formed during the decomposition of the OBB acid further combines with the HF and $BF_3$ thus rendering the catalyst unsuitable for recycling.

It is possible to limit the decomposition of the OBB acid by the extended heating of the complex under a vacuum at a lower temperature, such as 50° to 100° C., but the OBB acid will retain part of the catalyst which makes this process uneconomical. If the complex is heated at low temperatures in an inert solvent, it is not possible to recover all of the catalysts and it causes an important degradation of the OBB acid.

DISCLOSURE OF THE INVENTION

The process of the present invention resolves the problems presented by these previously described methods and allows practically complete recovery of the HF and $BF_3$ from the complex without degradation of the OBB acid.

The process of the present invention treats complexes of the general formula (I) with a solvent that is inert to the HF and $BF_3$ by the following procedure:

(a) mixing said complex with HF to form a solution;
(b) feeding said solution into a distillation column in which a solvent reflux was established;
(c) operating the column with a solvent reflux rate which is between about 5 and 40 times by weight of the feed delivery rate of the complex to the column;
(d) recovering the OBB acid from the boiler of the column; and
(e) recovering HF and $BF_3$ at the upper part of the column.

Suitable solvents for use in this process include halogenated aliphatic hydrocarbons and fluorinated aromatic hydrocarbons. In particular, methylene chloride and 1,2-dichloroethane provide advantageous results. The object of the present invention can be achieved, at best, when the solvent used has a high solubility for the OBB acid and a low solubility for the HF.

One way to minimize or substantially eliminate loss of HF and $BF_3$, in the process of the present invention is to operate a distillation column that has more than about eight theozetical peaks and preferably between about fifteen and forty theozetical peaks, while retaining as little as possible of the liquid and, operating with a solvent reflux wherein the delivery of solvent vapor is sufficient to assure dissociation of the complex, and vaporization of the HF.

The delivery of solvent vapor should be between about 5 and 40 times the amount, by weight, of the feed delivery of the complex to the column, and preferably between about 10 and 20 times the feed amount. The complex should preferably enter the column at a location in the top upper third of the column where the temperature is between about 20° C., which is the boiling point of anhydrous HF, and 150° C. The pressure in this area should range between 1 and 15 bars, i.e. equal to or slightly greater than atmospheric pressure. The column can contain a metal packing such as the MULTIKNIT type (registered trademark of Tissmetal Company) or a packing of stainless steel springs or rings.

The OBB acid, whether substituted or not, is recovered from the boiler of the column, and can be subsequently washed with water or an alkaline solution to eliminate any traces of HF and $BF_3$.

Further benefits and advantages of the invention will become apparent from a consideration of the following description given with reference to the accompanying figures which specify and show preferred embodiments of the invention.

FIG. 1 shows a process flow diagram of the continuous embodiment of the invention. The OBB acid, HF, $BF_3$ complex in a solution of HF is introduced into the column 1, by a pipe 2, while the solvent is heated to the boiling temperature range in a boiler 3. The solvent and HF vapors are condensed in a condenser 4, and the gaseous $BF_3$ leaves by a pipe 5. HF is separated from the solvent in a decanter 6 and is removed by a pipe 7 while the solvent is reintroduced at the top of the column 1 by a pipe 8. A tap 9 makes it possible to draw off small amounts of impurities such as $BF_3$ and HF hydrates which would otherwise accumulate in the decanter 6. The OBB acid in solution with the solvent is removed by a pipe 10 and washed with water in a vessel 11. The solvent is evaporated in an evaporator 12, and is reintroduced in the column by a pipe 13, while the molten OBB acid is removed by another pipe 14.

Figure 2:
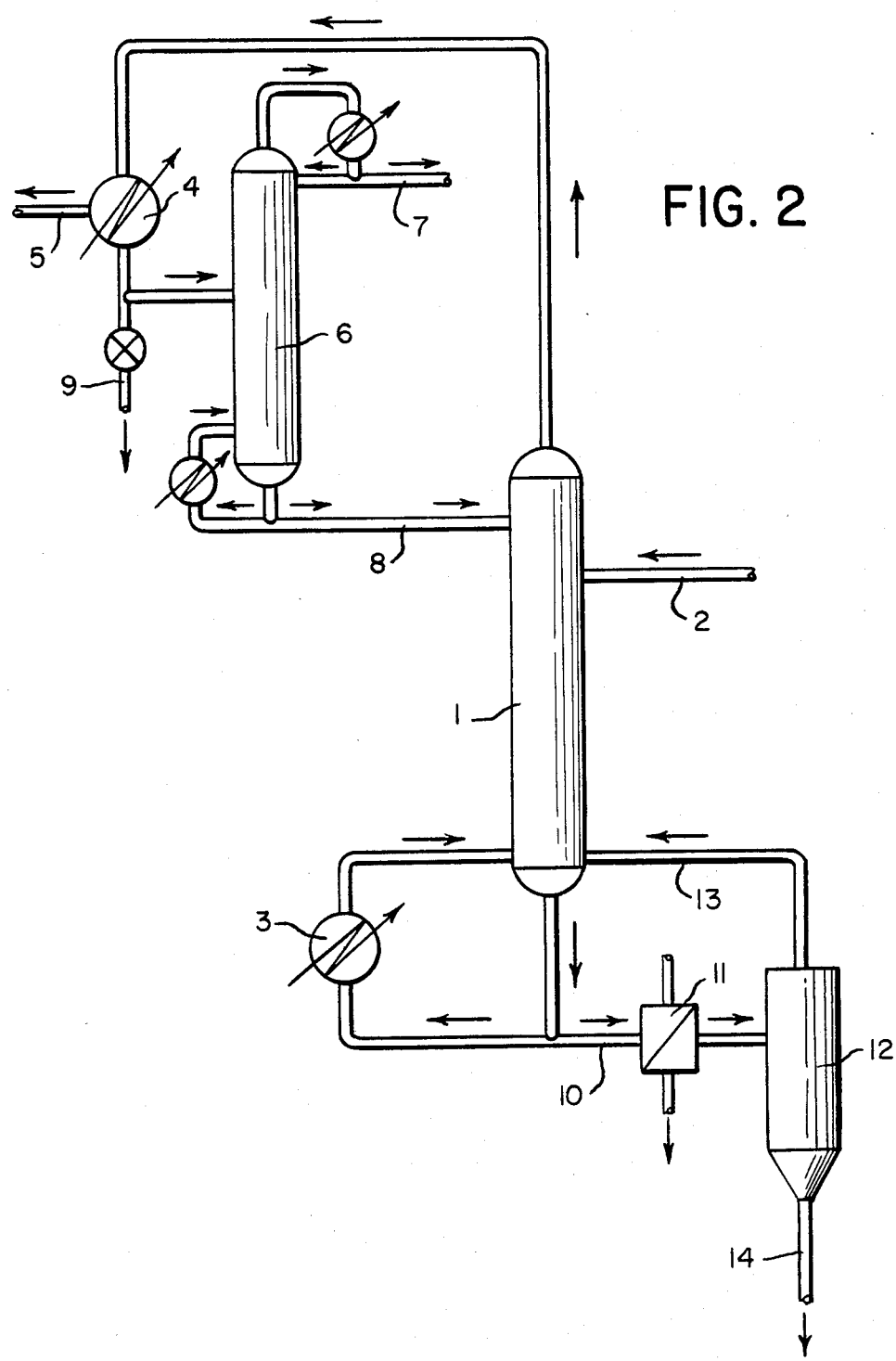

FIG. 2 is a process flow diagram for the embodiment of the invention wherein the HF is separated from the solvent by a different mode. The solvent and HF vapors are condensed in a condenser 4 and the gaseous $BF_3$ is taken off through pipe 5. The solvent and liquid HF are introduced into a separator 6 wherein the gaseous HF is removed by a pipe 7. The condensed solvent is removed at the foot of separator 6 and reintroduced into the column 1 by a pipe 8.

It is also possible to perform the decomposition of the OBB acid, HF, BF$_3$ complexes in two stages. This can be accomplished, for example, by feeding through a second column which operates under a pressure of 2 to 15 bars and a temperature range of 60° to 150° C., the partially decomposed complex coming from a first column which operates at atmospheric pressure or a partial vacuum at a temperature range between 40° and 60° C.

The scope of the invention is further described in connection with the following examples which are set forth for purposes of illustration only and are not to be construed as limiting the scope of the invention in any manner. It should be noted that the amounts or concentrations of OBB acid in the examples are determined analytically by liquid chromatography.

EXAMPLE 1

The OBB acid, HF, BF$_3$ complex is prepared according to U.S. Pat. No. 4,379,092 by reacting, in proportion, one mole phthalic anhydride, one mole benzene, ten moles HF, and ten moles BF$_3$. After degassing some of the BF$_3$ at −40° C., a solution of OBB acid complex and HF is obtained. This solution contains 203.3 g of OBB acid, 306.7 g of BF$_3$, a total of 200 g of HF, and 22.7 g of impurities from the reaction, for each mole of phthalic anhydride used.

A methylene chloride reflux was established in a stainless steel column. The column had an inside diameter of 38 mm and a height of 1.2 m, and was operated at a temperature of 41° C. at atmospheric pressure. The column contained stainless steel MULTIKNIT packing that had a porosity of 93.3% and a surface area of 215 dm$^2$/dm$^3$. The vaporization rate of methylene chloride in the boiler was 3.87 kg/h. 110 g complex solution was introduced into the column over a period of 28 minutes. The reflux was maintained for 20 minutes and the methylene chloride in the column boiler was evaporated. During the operation of the column, the gaseous BF$_3$ and HF were collected at the column head. Also, 0.5 g residue which contained a BF$_3$ hydrate was collected at the column head.

At the end of the operation, 33.3 g crude OBB acid, which contained 28.6 g OBB acid was collected, which represents a recovery yield of 93.8%. The crude OBB acid also contained 0.43 g BF$_3$ and 0.1 g HF. Therefore, efficiency for this decomplexing process was 99% for BF$_3$ and 99.6% for HF.

EXAMPLE 2

The process in this example was carried out in the same column and under the same temperature and pressure conditions as in Example 1. This time, the methylene chloride vaporization rate was 2.7 kg/hr. 94.6 g of the complex solution, prepared as described in Example 1, was introduced over a period of 42 minutes. After maintaining a reflux for 30 minutes, the solution collected in the boiler was cooled and then washed with 475 ml of distilled water. The solution was then evaporated to yield 29.6 g crude OBB acid which contained 26 g OBB for recovery yield of 99%.

The OBB acid was free of HF and BF$_3$ compounds, and the OBB decomplexing efficiency rate was 99% for BF$_3$ and 99.2% for HF. This rate took into account the amounts of BF$_3$ and HF recovered in the wash water of the solution after reflux.

EXAMPLE 3

The same column as described in Examples 1 and 2 was used. However, this time the process was carried out at atmospheric pressure and 84° C. Instead of methylene chloride, 1,2-dichloroethane was selected as the solvent. The dichloroethane vaporization rate was 4.22 kg/h. 110 g of the complex solution, which was prepared according to Example 1, was introduced into the column over a period of 22 minutes. The solvent reflux was maintained for 20 minutes before evaporating the dichloroethane contained in the boiler.

32 g crude OBB acid containing 28 g OBB acid was collected, and this corresponds to an OBB acid recovery yield of 92%. The crude OBB acid contained 0.33 g BF$_3$ and 0.1 g HF, which correspond to a decomplexing efficiency rate of 99.3% for BF$_3$ and 99.6% for HF.

EXAMPLE 4

A complex of ortho-(4-ethylbenzoyl)benzoic acid (OEBB acid) is prepared according to U.S. Pat. No. 4,379,092 by reacting 26.6 g phthalic anhydride, 19.07 g ethylbenzyne, 35.9 g HF, and 121.77 g BF$_3$ for 30 minutes at −40° C. After reaction and degassing at −40° C., 144.4 g of a complex solution in HF is obtained. This solution is injected over a 20 minute period into the column described in Example 1. The same temperature and pressure conditions were used and methylene chloride was again selected as the solvent. The methylene chloride reflux rate was 3.8 kg/h. After introducing the complex solution, the solvent reflux was maintained for 20 minutes before evaporating the solvent in the boiler. 43.31 g of crude OEBB acid which contained 39.07 g of OEBB acid was recovered. Also, the recovery rates for BF$_3$ and HF were 99.3% and 99.6%, respectively.

Having thus described our invention, what I claim as new and desire to secure by Letters Patent are:

1. A process for the decomposition of complexes of ortho-benzoyl benzoic acid hydrogen fluoride, and boron trifluoride of the general formula:

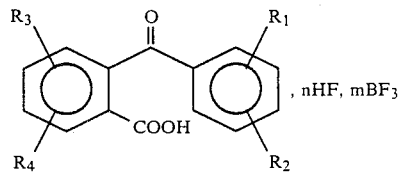

, nHF, mBF$_3$ wherein R$_1$, R$_2$, R$_3$, and R$_4$ represent hydrogen, a halogen atom, or a straight or branched chain alkyl group having 1 to 5 carbon atoms, and n and m are any integer from 1 to 6, to obtain ortho-benzoyl benzoic acid separate from hydrogen fluoride and boron trifluoride, in high yield which comprises:
   (a) mixing said complex with HF to form a solution;
   (b) feeding said solution into a distillation column having more than eight theoretical plates and in which a solvent reflux is established at a location in the top upper third of said column where the temperature is between 20° and 150° C. and the pressure is between 1 and 15 bars;
   (c) operating said column with a solvent feed rate which is between about 5 and 40 times by weight of the feed rate of said solution to the column;
   (d) recovering the ortho-benzoyl benzoic acid by evaporating any solvent present with said acid in the boiler of the column; and (e) recovering HF, BF$_3$, and solvent vapors at the upper part of the column;
(f) separating BF$_3$ from the recovered compounds of step (e) by condensing the HF and solvent;
(g) separating HF from the solvent; and
(h) recycling the solvent back to the column.

2. The process according to claim 1 wherein the solvent is a halogenated aliphatic hydrocarbon.

3. The process according to claim 1 wherein the solvent is a fluorinated aromatic hydrocarbon.

4. The process according to claim 2 wherein the solvent is methylene chloride.

5. The process according to claim 2 wherein the solvent is 1,2-dichloroethane.

6. The process according to claim 1 wherein said solvent reflux rate is between about 10 and 20 times by weight the feed delivery rate of the complex to the column.

7. The process according to claim 1 wherein the recovered ortho-benzoyl benzoic acid is subsequently worked with water or an alkaline solution to remove any trace of HF and BF$_3$.

8. The process according to claim 1 wherein the column has 15 to 40 theoretical plates.

9. A process for the decomposition of complexes of ortho-benzoyl benzoic acid, hydrogen fluoride, and boron trifluoride of the general formula:

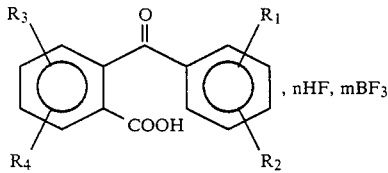
, nHF, mBF$_3$ wherein R$_1$, R$_2$, R$_3$, and R$_4$ represent hydrogen, a halogen atom, or a straight or branched chain alkyl group having 1 to 5 carbon atoms, and n and m are any integer from 1 to 6, to obtain ortho-benzoyl benzoic acid separate from hydrogen fluoride and boron trifluoride, in high yield which comprises:
(a) mixing said complex with HF to form a solution;
(b) feeding said solution into the top upper third of a distillation column;
(c) operating said column with a solvent feed rate which is sufficient to assure dissociation of the complex and vaporization of the HF;
(d) evaporating the solvent without decomposing the OBB acid to recover said acid; and
(e) recovering HF, BF$_3$ and solvent vapors from the top of the column.

10. The process according to claim 9 further comprising separating the HF, BF$_3$ and solvent and recycling the solvent to said column.

11. The process according to claim 9 wherein the solvent is a halogenated aliphatic hydrocarbon or a fluorinated aromatic hydrocarbon.

12. The process according to claim 11 wherein the solvent is methylene chloride or 1,2-dichloroethane.

13. The process according to claim 9 wherein the column is operated at a temperature between 20° and 150° C. and at a pressure of between 1 to 15 bars; said column further comprising at least eight or more theoretical plates, and a solvent reflux rate which is between about 5 and 40 times by weight of the feed delivery rate of the complex solution to the column.

14. The process according to claim 13 wherein the number of theoretical plates is between 15 and 40 and the solvent feed rate to the column is between about 10 and 20 times the feed rate of the solution to the column.

15. The process according to claim 9 further comprising treating the recovered ortho-benzoyl benzoic acid with water or an alkaline solution to remove any remaining traces of HF or BF$_3$.

16. A process for recovering ortho-benzoyl benzoic acid in high yield from a complex of ortho-benzoyl-benzoic acid, hydrogen fluoride, and boron trifluoride of the general formula:

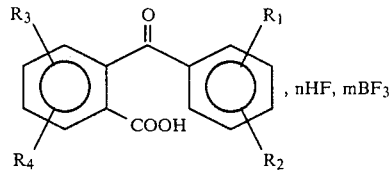
, nHF, mBF$_3$ wherein R$_1$, R$_2$, R$_3$, and R$_4$ represent hydrogen, a halogen atom, or a straight or branched chain alkyl group having 1 to 5 carbon atoms, and n and m are any integer from 1 to 6, which comprises:
(a) mixing said complex with HF to form a solution;
(b) feeding said solution into a distillation column with a suitable solvent wherein the delivery of the solvent vapor is sufficient to assure dissociation of the complex and vaporization of the HF;
(c) operating said column with a solvent reflux;
(d) recovering ortho-benzoyl benzoic acid from the column boiler and
(e) recovering said HF, BF$_3$, and solvent from the upper part of the column.

17. The process according to claim 16 further comprising separating the HF, BF$_3$ and solvent and recycling the solvent to said column.

18. The process according to claim 16 wherein the solvent is a halogenated aliphatic hydrocarbon or a fluorinated aromatic hydrocarbon.

19. The process according to claim 18 wherein the solvent is methylene chloride or 1,2-dichloroethane.

20. The process according to claim 16 wherein the column is operated at a temperature between 20° and 150° C. and at a pressure of between 1 and 15 bars; said column further comprising at least eight or more theoretical plates, and a solvent reflux rate which is between about 5 and 40 times by weight of the feed delivery rate of the complex solution to the column.

21. The process according to claim 20 wherein the number of theoretical plates is between 15 and 40 and the solvent feed rate to the column is between about 10 and 20 times the feed rate of the solution to the column.

22. The process according to claim 16 further comprising treating the recovered ortho-benzoyl benzoic acid with water or an alkaline solution to remove any remaining traces of HF or BF$_3$.

* * * * *